(12) United States Patent
Tuijthof et al.

(10) Patent No.: US 10,064,640 B2
(45) Date of Patent: Sep. 4, 2018

(54) SURGICAL DEVICE, IN PARTICULAR FOR MINIMALLY INVASIVE SURGERY

(71) Applicant: Technische Universiteit Delft, Delft (NL)

(72) Inventors: Gabrielle Josephine Maria Tuijthof, Delft (NL); Tim Horeman, Delft (NL)

(73) Assignee: TECHNISCHE UNIVERSITEIT DELFT, Delft (NL)

( * ) Notice: Subject to any disclaimer, the term of this patent is extended or adjusted under 35 U.S.C. 154(b) by 402 days.

(21) Appl. No.: 14/859,952

(22) Filed: Sep. 21, 2015

(65) Prior Publication Data

US 2016/0008019 A1    Jan. 14, 2016

Related U.S. Application Data

(63) Continuation of application No. PCT/NL2014/050166, filed on Mar. 20, 2014.

(30) Foreign Application Priority Data

Mar. 21, 2013    (NL) ..................................... 2010498

(51) Int. Cl.
*A61B 17/00* (2006.01)
*A61B 17/29* (2006.01)

(52) U.S. Cl.
CPC .... *A61B 17/29* (2013.01); *A61B 2017/00327* (2013.01); *A61B 2017/00367* (2013.01);
(Continued)

(58) Field of Classification Search
CPC .............. A61B 17/29; A61B 17/32053; A61B 17/32003; A61B 17/0469; A61B 17/04; A61B 17/0491; A61B 17/3468; A61B 2017/00327; A61B 2017/00367; A61B 2017/00991; A61B 2017/2901; A61B 2017/2903; A61B 2017/2931; A61B 2017/32004; A61B 2017/320064; A61B 2017/00685; A61B 2017/2936;
(Continued)

(56) References Cited

U.S. PATENT DOCUMENTS 5,471,992 A    12/1995    Banik et al.
5,921,956 A    7/1999    Grinberg et al.
(Continued)

FOREIGN PATENT DOCUMENTS

WO    2008/045361    4/2008
WO    2014/148898    9/2014

*Primary Examiner* — Elizabeth Houston
*Assistant Examiner* — Mohamed Gabr
(74) *Attorney, Agent, or Firm* — Peacock Law P.C.; Janeen Vilven; Camille Martinez

(57) ABSTRACT

A surgical device with a shaft having a distal end to which a surgical instrument is mountable and a proximal end equipped for handling the instrument, wherein the shaft is hollow and the surgical instrument is mountable on inserts that are longitudinally movable in the shaft parallel to the longitudinal axis and that are diametrically opposed to each other. The shaft comprises outer and inner tubes rotatable in opposite directions with respect to the longitudinal axis, and the inserts are coupled to the outer and inner tubes to convert rotational movement of the tubes into longitudinal movement of the inserts.

12 Claims, 2 Drawing Sheets

(52) U.S. Cl.
CPC ........... *A61B 2017/00991* (2013.01); *A61B 2017/2901* (2013.01); *A61B 2017/2903* (2013.01); *A61B 2017/2931* (2013.01)

(58) Field of Classification Search
CPC .. A61B 2017/00323; A61B 2017/0046; A61B 10/0275; A61B 10/06; A61B 10/025; A61B 2217/007; A61B 2010/0208; A61B 2017/00473; A61B 2017/2902; A61F 9/0008; A61M 2210/0612; A61M 3/0279; A61M 5/3286
See application file for complete search history.

(56) References Cited

U.S. PATENT DOCUMENTS

| | | |
|---|---|---|
| 2008/0275301 A1 | 11/2008 | Lubowski |
| 2010/0010512 A1* | 1/2010 | Taylor .................. A61B 17/04 606/144 |
| 2013/0030408 A1 | 1/2013 | Piferi et al. |

* cited by examiner

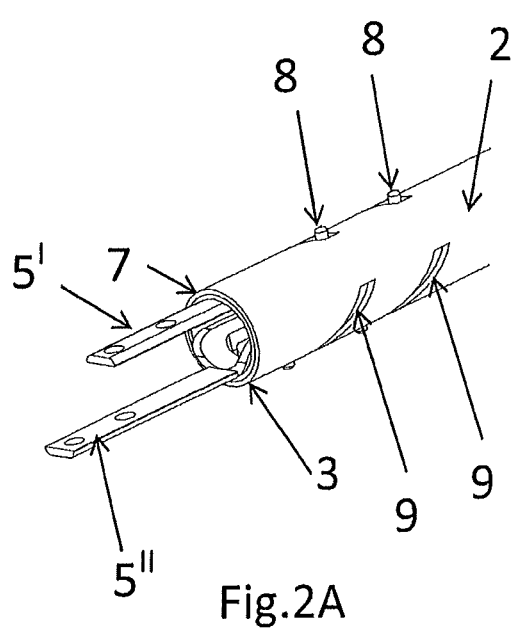
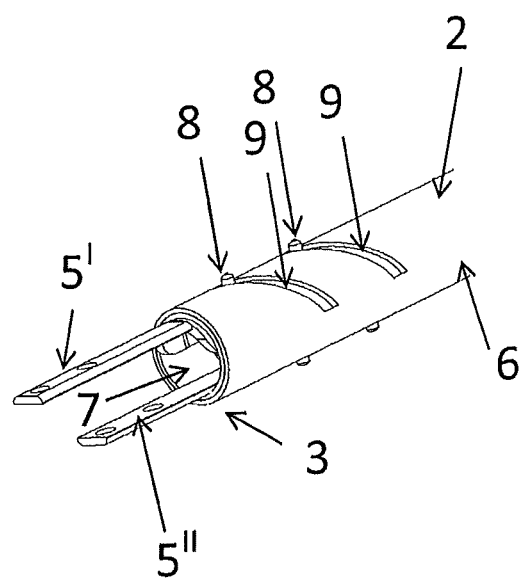
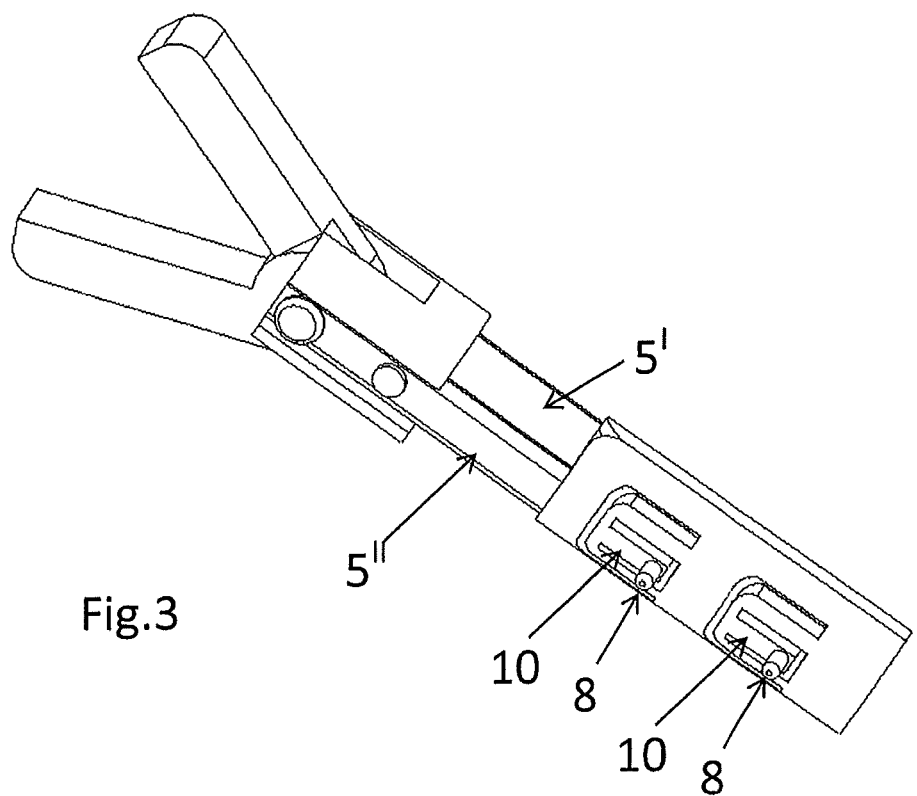

SURGICAL DEVICE, IN PARTICULAR FOR MINIMALLY INVASIVE SURGERY

CROSS-REFERENCE TO RELATED APPLICATIONS

This application is a continuation application of Patent Cooperation Treaty Application No. PCT/NL2014/050166, entitled "Surgical Device, in Particular for Minimally Invasive Surgery", filed on Mar. 20, 2014, which claims priority to Netherlands Patent Application No. 2010498, filed on Mar. 21, 2013, and the specifications and claims thereof are incorporated herein by reference.

STATEMENT REGARDING FEDERALLY SPONSORED RESEARCH OR DEVELOPMENT

Not Applicable.

INCORPORATION BY REFERENCE OF MATERIAL SUBMITTED ON A COMPACT DISC

Not Applicable.

COPYRIGHTED MATERIAL

Not Applicable.

BACKGROUND OF THE INVENTION

Field of the Invention (Technical Field)

The present invention relates to a surgical device, in particular for minimally invasive surgery, provided with a shaft having a distal end to which a surgical instrument is mounted or mountable and a proximal end equipped for handling the instrument.

Description of Related Art

U.S. Pat. No. 5,471,992 discloses an instrument for obtaining a tissue sample from a site deep within a patient's body. The instrument is provided with a shaft having a distal end to which a jaw lime member is mounted for taking the tissue sample, and a proximal end equipped for handling the jaw lime member. The shaft is at least in part hollow and the jaw lime member is mounted on inserts that are longitudinally movable in said shaft parallel to the longitudinal axis of the shaft, and said inserts are provided diametrically opposed to each other within the shaft.

As minimally invasive operations are performed through small portals and the manipulation possibilities of the known surgical instruments are limited, gaining access to the pathology site can be challenging. This is especially true for body cavities with confined spaces and few available access portals such as the human knee or ankle joint. On top of that, the tissue located in these particular body cavities (cartilage, ligaments) are typically much tougher to machine (cut, punch) than in other areas of the human body, such as those in the abdominal area. As a result, a number of problems exist. The confined space wherein a known surgical device with relatively poor manipulation properties is used causes an undesirable extension of the operation time, as surgeons are forced to interchange several instruments to cut the target tissue entirely. Moreover, healthy tissues are at risk, because surgeons can accidentally load the tissue surrounding the access portals too strongly in their efforts to reach the pathologic area. Further there is the risk that the surgeon introduces more bacteria in the body cavity when required to frequently exchange the cutting instruments, and to damage tissues when inserting instruments as this process is performed blindly. Finally, surgeons can develop health problems related to the used instruments with poor maneuverability, such as blisters, muscle soreness, fatigue, and early signs of arthritis.

The invention intends to address these problems and proposes for this purpose a surgical device and a separate shaft for such a surgical device, having the features of one or more of the appended claims.

BRIEF SUMMARY OF THE INVENTION

Objects, advantages and novel features, and further scope of applicability of the present invention will be set forth in part in the detailed description to follow, taken in conjunction with the accompanying drawings, and in part will become apparent to those skilled in the art upon examination of the following, or may be learned by practice of the invention. The objects and advantages of the invention may be realized and attained by means of the instrumentalities and combinations particularly pointed out in the appended claims.

BRIEF DESCRIPTION OF THE SEVERAL VIEWS OF THE DRAWINGS

The accompanying drawings, which are incorporated into and form a part of the specification, illustrate one or more embodiments of the present invention and, together with the description, serve to explain the principles of the invention. The drawings are only for the purpose of illustrating one or more preferred embodiments of the invention and are not to be construed as limiting the invention. In the drawings:

FIGS. 2A and 2B show the distal end of the surgical device of the invention without surgical instrument mounted thereon;

FIG. 3 shows the inserts of the surgical device of the invention with a gripping instrument mounted thereon;

DETAILED DESCRIPTION OF THE INVENTION

Figure 1:
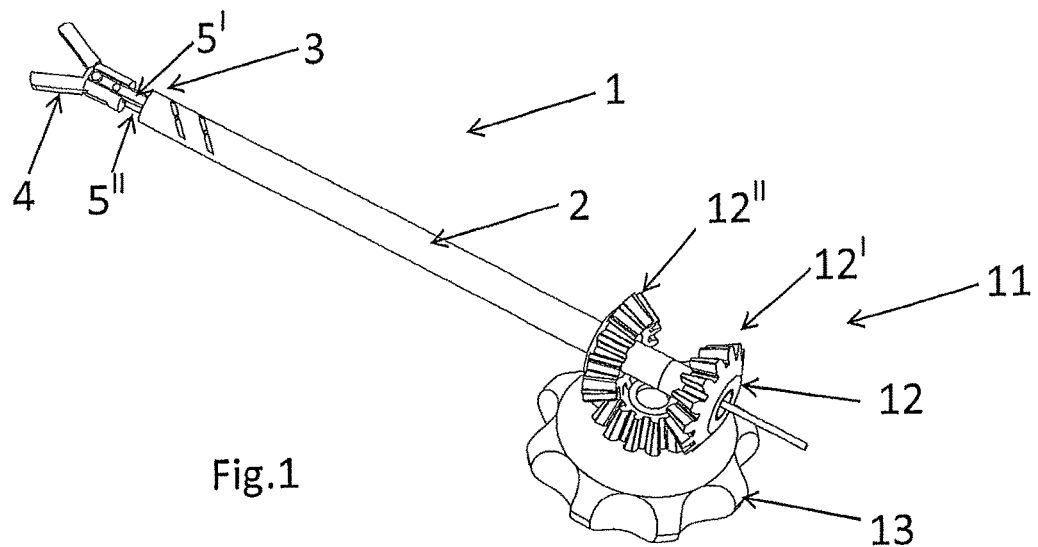
FIG. 1 schematically shows the surgical device of the invention.

In a first aspect of the invention the shaft of the surgical device comprises an outer tube and an inner tube which are rotatable in opposite directions with respect to the longitudinal axis of the shaft, and the inserts are coupled to the outer tube and the inner tube so as to convert rotational movement of said tubes into longitudinal movement of the inserts. By mounting the surgical instrument on the inserts, the instrument tip can be oriented in longitudinal orientation relative to the shaft of the surgical device for safe and easy insertion through an access portal in a body portion of the patient, whilst the rotation of the outer tube and inner tube with respect to each other enables the transfer of high forces to the inserts, and consequently to the surgical instrument mounted or mountable thereon. Once inside the body cavity, the instrument tip can be moved left to right and back to reach all areas of pathologic tissue by manipulating the longitudinal position of the inserts with reference to the shaft. This allows the surgeon to keep the instrument tip continuously in sight and perform precise tissue cutting, wherein the cutting process can be executed uninterruptedly since instrument exchanges are avoided. This contributes to increased patient safety and increased surgical efficiency. A notable benefit of the surgical device of the invention is that it provides a very stiff support to the surgical instrument mounted thereon in any feasible position of said instrument.

The accuracy of the surgical device of the invention is promoted when the inner tube snugly fits into the outer tube.

Advantageously the inserts have one or more protrusions cooperating with slits in the shaft so as to define the longitudinal position of the inserts with respect to the shaft. The slits can be provided at a preselected angle with reference to the shaft's longitudinal direction so as to accommodate to the desired conversion of forces caused by the rotational movement of the outer tube and the inner tube to the forces that are thereby transferred to the inserts.

It is preferred that the slits are provided in the outer tube and inner tube of the shaft, and more in particular that the slits are provided in the outer tube and inner tube at a predetermined angle with respect to each other so as to arrange that each protrusion on the inserts has a single position at which it is able to protrude through both a slit in the inner tube and through a slit in the outer tube. This again promotes the mechanical accuracy of the surgical device as well as the accuracy of controlling the position of the surgical instrument mounted at the distal end of the surgical device. A beneficial arrangement of this construction is that rotation of the inner tube and the outer tube with respect to each other causes each protrusion on the inserts that protrudes through the angled slits in the inner tube and outer tube respectively to translate in the shaft's longitudinal direction. The translation of the protrusions on the inserts results in a corresponding translation of said inserts, and this results in a corresponding movement and manipulation of the surgical instrument that is mounted on the inserts.

Another aspect of the surgical device of the invention is that preferably the inserts are provided with protrusions mounted or provided on resilient parts of said inserts so as to arrange that the protrusions can be depressed and removed from the slits in the shaft. This enables an easy and swift replacement of the inserts and the surgical instrument mounted thereon, which is beneficial for the surgical instrument's cleaning and sterilization after completion of the surgical operation.

To enable its proper handling the surgical device has at its proximal end means for rotational movement of the inner tube and outer tube of the shaft with respect to each other. This can be implemented in several ways, for instance with arms connected to the inner tube and outer tube for their relative rotation. It is in a particular embodiment however preferred that the means for rotational movement of the inner tube and outer tube comprise a differential gear coupled at its opposite ends with the inner tube and outer tube respectively.

The invention is also embodied in a separate shaft as described as part of the surgical device of the invention. Such a loose shaft can be part of a replacement kit and warrants that it receives independent protection, and not merely as part of the surgical device of the invention.

The invention will hereinafter be further elucidated with reference to the attached drawings of an exemplary embodiment of the surgical device of the invention, which is deemed not to be limiting as to the appended claims.

With reference first to FIG. 1, the surgical device 1 of the invention is shown schematically. This surgical device 1 is particularly intended for minimally invasive surgery, and is provided with a shaft 2 having a distal end 3 to which a surgical instrument 4 is mounted or mountable and a proximal end 11 equipped for handling the instrument 4. The surgical device 1 according to the invention has a hollow shaft 2, which enables that wires or rods can be arranged within the hollow shaft 2 to control the instrument 4. According to the invention the instrument's position is however determined in the manner elucidated hereinafter.

The surgical instrument 4 is mounted or mountable on inserts 5', 5" that are longitudinally movable in the said shaft 2 parallel to the longitudinal axis of the shaft 2, which inserts 5', 5" are provided diametrically opposed to each other within said shaft 2. This is clearly shown in FIGS. 2A and 2B showing the inserts 5', 5" without instrument mounted thereon.

The shaft 2 comprises an outer tube 6 and an inner tube 7 which are rotatable in opposite directions with respect to the longitudinal axis of the shaft 2. Preferably the inner tube 7 snugly fits into the outer tube 6 as is shown in FIGS. 2A and 2B.

Figures 4, 5:
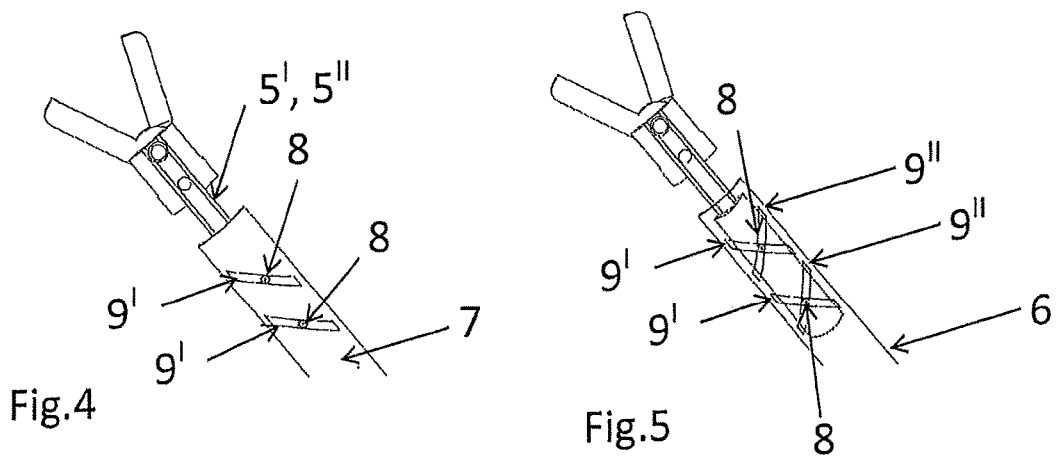
FIG. 4 shows the inserts and instrument of FIG. 3 and additionally an inner tube of the surgical device of the invention.
FIG. 5 shows the inserts, the instrument and the inner tube of FIG. 4 and additionally an outer tube of the surgical device of the invention.

The inserts 5', 5" are coupled to the outer tube 6 and the inner tube 7 so as to convert rotational movement of said tubes 6, 7 into longitudinal movement of the inserts 5', 5". This is preferably done by arranging that the inserts 5', 5" have one or more protrusions 8 cooperating with slits 9 in the shaft 2, in particular in the outer tube 6 and inner tube 7 of the shaft 2, so as to define the longitudinal position of the inserts 5', 5" with respect to the shaft 2. By rotation of the outer tube 6 and inner tube 7 with respect to each other the protrusions 8 are moved by the slits 9, causing that the inserts 5', 5" assume different positions as shown in FIGS. 2A and 2B respectively. It is noted that the inserts 5', 5" do not rotate with the outer tube 6 or inner tube 7, but are rotationally stationary. This is possible because the slits are provided in the outer tube 6 and inner tube 7 at a predetermined angle with respect to each other so as to arrange that each protrusion 8 on the inserts 5', 5" has a single position at which it is able to protrude through both a slit in the inner tube 7 and a slit in the outer tube 6. This can be best understood with reference to FIGS. 4 and 5. FIG. 4 shows the inserts 5', 5" within the inner tube 7 only, with the protrusions 8 of the inserts 5', 5" extending through the slits 9' of the inner tube 7. In FIG. 5 also the outer tube 6 is shown, and from this figure it is clear that the protrusions 8 also extend through the angled slits 9" of the outer tube 6, which slits 9" may for instance be at an angle of 90° with respect to the slits 9' of the inner tube 7. This construction of the slits 9', 9" in the inner tube 7 and outer tube 6 arranges that for each combination of slits 9', 9" there is a single and unique position that the protrusion 8 that is assigned to these slits 9', 9" can assume, being at the crossing of the slits 9', 9". When the outer tube 6 and the inner tube 7 are rotated with respect to each other this crossing of the slits 9', 9" undergoes a translational displacement in the longitudinal direction of the shaft 2. Likewise the corresponding protrusions 8 on the inserts 5', 5" make the same movement and cause that the respective inserts 5', 5" follow this translational movement. In other words: rotation of the inner tube 7 and the outer tube 6 with respect to each other causes each protrusion 8 on the inserts 5', 5" that protrudes through the angled slits 9', 9" in the inner tube 7 and outer tube 6 respectively to translate in the shaft's longitudinal direction, without rotation of the inserts 5', 5" themselves.

FIG. 3 shows that the inserts 5', 5" are provided with protrusions 8 on resilient parts 10 of said inserts 5', 5" so as to arrange that the protrusions 8 can be depressed and removed from the slits 9', 9" in the inner tube 7 and outer tube 6 of the shaft.

Returning to FIG. 1 it is shown that at its proximal end 11, the surgical device 1 has means 12 to cause rotational movement of the inner tube and outer tube of the shaft 2 with respect to each other. These means 12 for rotational movement of the inner tube and outer tube comprise a differential gear 12', 12" coupled at its opposite ends with the inner tube and outer tube respectively. The way this may be construed is clear for the skilled person and needs no further elucidation with reference to the drawing. The figure shows also a knob 13 which may be used to drive the differential gear 12', 12".

The inventors explicitly remark that the above given elucidation with reference to the drawing is provided with reference to a very schematically displayed surgical device, which is only intended to explain the principles of the invention without intent to limit the claims to what is exactly shown in the drawing. The skilled person understands that numerous variations are feasible to this schematic embodiment without departing from the invention as defined by the appended claims.

What is claimed is:

1. A surgical device, in particular for minimally invasive surgery, provided with:
   a shaft having a distal end equipped to mount a surgical instrument on the distal end, said distal end of the shaft comprising inserts, and a proximal end equipped for handling the instrument,
   wherein the shaft is at least in part hollow, and
   wherein the surgical instrument is equipped to be mounted on the inserts, which are longitudinally movable in the shaft parallel to the longitudinal axis of the shaft,
   wherein the inserts are provided diametrically opposed to each other within the shaft,
   wherein the shaft comprises an outer tube and an inner tube which are rotatable in opposite directions with respect to the longitudinal axis of the shaft, and the inserts are coupled to the outer tube and the inner tube so as to convert rotational movement of said tubes into longitudinal movement of the inserts,
   wherein the inserts have one or more protrusions cooperating with slits in the outer tube and slits in the inner tube so as to define the longitudinal position of the inserts with respect to the shaft,
   wherein the slits in the outer tube and the slits in the inner tube are provided at a predetermined angle with respect to each other so as to arrange that each protrusion of the one or more protrusions on the inserts has a single position at which each protrusion is able to protrude through both a slit in the inner tube and a slit in the outer tube.

2. The surgical device according to claim 1, wherein the inner tube snugly fits into the outer tube.

3. The surgical device according to claim 1 or 2, wherein rotation of the inner tube and the outer tube with respect to each other causes each protrusion on the inserts that protrudes through the angled slits in the inner tube and outer tube respectively to translate in the shaft's longitudinal direction.

4. The surgical device according to claim 1, wherein the one or more protrusions on the inserts are provided on resilient parts of said inserts so as to arrange that the one or more protrusions can be depressed and removed from the slits in the shaft.

5. The surgical device according to claim 1, wherein at the proximal end the device has means for rotational movement of the inner tube and outer tube of the shaft with respect to each other.

6. The surgical device according to claim 5, wherein the means for rotational movement of the inner tube and outer tube comprise a differential gear coupled at its opposite ends with the inner tube and outer tube respectively.

7. A shaft for a surgical instrument, comprising:
   a proximal end and a distal end equipped to mount the surgical instrument thereon,
   wherein the shaft is at least in part hollow and is equipped to receive inserts diametrically opposed to each other within said shaft, and
   wherein the surgical instrument is mounted or mountable on said inserts, and wherein the shaft is arranged such that the inserts are longitudinally movable in said shaft parallel to the longitudinal axis of the shaft,
   wherein the shaft comprises an outer tube and an inner tube which are rotatable in opposite directions with respect to the longitudinal axis of the shaft, and the inserts are coupled to the outer tube and the inner tube so as to convert rotational movement of said tubes into longitudinal movement of the inserts,
   wherein the inserts have one or more protrusions cooperating with slits in the outer tube and slits in the inner tube so as to define the longitudinal position of the inserts with respect to the shaft, wherein the slits in the outer tube and the slits in the inner tube are provided at a predetermined angle with respect to each other so as to arrange that each protrusion of the one or more protrusions on the inserts has a single position at which each protrusion is able to protrude through both a slit in the inner tube and a slit in the outer tube.

8. The shaft according to claim 7, wherein the inner tube snugly fits into the outer tube.

9. The shaft according to claim 7, wherein the slits are provided in the outer tube and inner tube of the shaft.

10. The shaft according to claim 7, wherein rotation of the inner tube and the outer tube with respect to each other causes each protrusion on the inserts that protrudes through the angled slits in the inner tube and outer tube respectively to translate in the shaft's longitudinal direction.

11. The shaft according to claim 7, wherein the one or more protrusions on the inserts are provided on resilient parts of said inserts so as to arrange that the one or more protrusions can be depressed and removed from the slits in the shaft.

12. The shaft according to claim 7, wherein at the proximal end the shaft is connectable to means for rotational movement of the inner tube and outer tube of the shaft with respect to each other.

\* \* \* \* \*